United States Patent [19]

Fulwyler

[11] Patent Number: 4,717,655

[45] Date of Patent: Jan. 5, 1988

[54] METHOD AND APPARATUS FOR DISTINGUISHING MULTIPLE SUBPOPULATIONS OF CELLS

[75] Inventor: Mack J. Fulwyler, Sunnyvale, Calif.

[73] Assignee: Becton, Dickinson and Company, Franklin Lakes, N.J.

[21] Appl. No.: 660,993

[22] Filed: Oct. 15, 1984

Related U.S. Application Data

[62] Division of Ser. No. 412,648, Aug. 30, 1982, Pat. No. 4,499,052.

[51] Int. Cl.⁴ .............. G01N 33/53; G01N 33/554; C12Q 1/04; C12Q 1/06
[52] U.S. Cl. ............................. 435/7; 435/34; 435/39; 436/519; 436/534; 436/547; 436/800
[58] Field of Search .............. 435/30, 34, 39, 7; 436/519, 523, 528, 533, 534, 800, 547; 424/3, 7.1; 356/39; 250/461.2

[56] References Cited

U.S. PATENT DOCUMENTS

| 3,916,197 | 10/1975 | Fulwyler | 250/461.2 X |
|---|---|---|---|
| 3,916,205 | 10/1975 | Kleinerman | 356/36 X |
| 4,169,137 | 9/1979 | Hirschfeld | 424/3 X |
| 4,243,318 | 1/1981 | Stohr | 356/39 |
| 4,284,412 | 8/1981 | Hansen et al. | 436/519 X |
| 4,510,244 | 4/1985 | Parks et al. | 436/519 X |
| 4,599,307 | 7/1986 | Saunders et al. | 435/34 |

*Primary Examiner*—Sidney Marantz
*Assistant Examiner*—Randall E. Deck
*Attorney, Agent, or Firm*—Richard J. Rodrick

[57] ABSTRACT

A method of distinguishing multiple subpopulations of cells from a single sample of cells of a variety of types comprises labeling particles with two or more marking agents. These particles are marked in a plurality of different pre-selected ratios of the agents ranging between zero percent and one hundred percent of each agent. Each such agent has distinguishing, quantifiable marking characteristics. The differently labeled particles are mixed with cells suspected of having specific receptors for the differently labeled particles. Each cell is analyzed to determine the ratio of any two identifiable marking characteristics associated with each cell so that is can be classified in a subpopulation category if its ratio of marking characteristics is related to one of the pre-selected ratios of marking agents.

An apparatus for carrying out the above-described method is also within the purview of the present invention.

10 Claims, 2 Drawing Figures

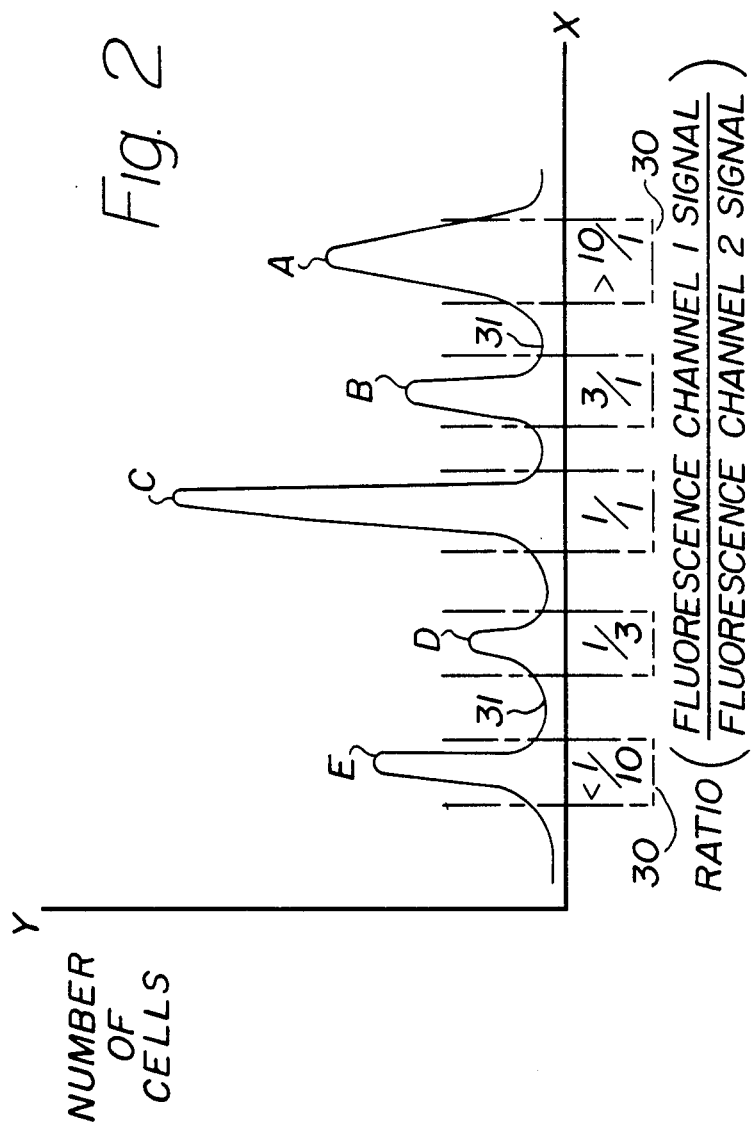

METHOD AND APPARATUS FOR DISTINGUISHING MULTIPLE SUBPOPULATIONS OF CELLS

This is a division, of application Ser. No. 412,648, filed Aug. 30, 1982, now U.S. Pat. No. 4,499,052.

BACKGROUND OF THE INVENTION

1. Field of the Invention

The present invention relates to a method and apparatus for distinguishing multiple subpopulations of particles, and more particularly, concerns a method and apparatus for simultaneously distinguishing and enumerating multiple subpopulations of cells which have been labeled with different fluorochromes.

2. Description of the Prior Art

Presently known and available flow-through cytometers and the like particular detecting devices commonly include two channels for the detection of two subpopulations of cells in a mixture. For example, devices are known which include two fluorescence channels which can detect cells specifically labeled with two fluorescent agents associated with the respective fluorescence channels. In these type devices, a complete fluorescence channel including the electrical circuitry and fluorescence detectors has been required for each fluorochrome-treated cell to be detected in the mixture of cells in the sample being analyzed. Therefore, in order to detect multiple subpopulations of cells in a sample using flow-through cytometry, an equivalent number of fluorescence channels is required using the known, conventional devices. A further limitation is that the nature of excitation and emission characteristics of fluorochromes makes it difficult to acquire more than two fluorochromes, attachable to protein, which provide emissions sufficiently separated in wavelength. Some representative devices using conventional flow-through cytometry are described in U.S. Pat. Nos. 4,198,160; 3,738,759; 3,864,571; and in "A Proposal for an Automatic Multi-parameter Analyzer for Cells (AMAC)," by Robert C. Leif, *Automated Cell Identification and Cell Sorting*, edited by George L. Wied, Academic Press, New York 1970, pages 131–159.

There are many instances when it is desirable to be able to detect multiple subpopulations of cells from a sample mixture. However, as alluded to above, one of the disadvantages found in conventional equipment is that plurality of fluorochromes would have to be employed for labeling the cells, as well as an equivalent number of fluorescence channels to monitor the specific spectral characteristics associated with the individual fluorochromes. Moreover, a sufficient plurality of fluorochromes is not presently available. Clearly, this has created formidable problems. While it is desirable to be able to detect, and also enumerate, multiple subpopulations of cells from a sample mixture, it is even more desirable to minimize the number of fluorochromes employed as well as the number of fluorescence channels and the associated circuitry. With this in mind, the present invention is directed to solving the aforementioned problem, while satisfying the desired need for the determination of multiple subpopulations of cells from a sample mixture.

SUMMARY OF THE INVENTION

A method of distinguishing multiple subpopulations of particles from a single sample of particles of a variety of types includes labeling receptive substances with two or more marking agents in a plurality of different pre-selected ratios of said agents. The ratios may range between zero percent and one hundred percent of each agent which has a distinguishing and quantifiable marking characteristic. This method further includes mixing the differently labeled substances with particles suspected of having specific receptors for the differently labeled substances. Each particle is analyzed to determine the ratio of the two identifiable marking characteristics associated with each particle. Thereafter, each particle can be classified in a subpopulation category if its ratio of marking characteristics is related to one of the pre-selected ratios of marking agents.

In a preferred embodiment of this aspect of the present invention, the method includes labeling antibody proteins with two fluorochromes in a plurality of different pre-selected ratios. Each fluorochrome has distinct emission spectra. Excitation energy is provided to the cells by flow-through cytometry techniques to thereby excite both types of the fluorochromes. Each cell is analyzed to determine the fluorescence emitted by both excited fluorochromes to thereby establish the ratio of the fluorescence emissions. Thereafter, each cell is classified by subpopulation category if related to one of the pre-selected ratios of labeled antibody proteins. Simultaneous enumeration of the cell subpopulations can also be achieved with the present invention.

Another aspect of the present invention is an apparatus for distinguishing multiple subpopulations of particles from a sample of particles flowing in a liquid path. The particles have been labeled with up to two or more different marking agents having distinguishing and quantifiable characteristics. The apparatus includes means for separately detecting the quantifiable characteristics associated with each particle and determining a ratio of any two quantifiable characteristics thereof. Means for recording the ratios is provided so that the particles can be classified into a plurality of subpopulation categories.

In a preferred embodiment of this aspect of the present invention, the apparatus simultaneously distinguishes and enumerates multiple subpopulations of cells which have been labeled with up to two or more different fluorochromes. Means for exciting fluorochromes on each cell as it flows in a liquid path is provided. This preferred apparatus further includes means for separately detecting the quantity of fluorescence emitted by the two different fluorochromes associated with each cell and determining the ratio of fluorescence quantities of the two fluorochromes. Further, there is means for displaying the ratios so that the cells can be classified into a plurality of subpopulation categories and enumerated.

It is also within the purview of the present invention to determine ratios of fluorescenated particles having similar emission characteristics, but different excitation characteristics. Different light sources for excitation might be required, while only one fluorescence detector need be employed. Also, ratios may be determined in accordance with the present invention utilizing fluorescenated particles having both different excitation and emission characteristics.

In accordance with the principles of the present invention, a number of advantages and objectives are attained. Primarily, the present invention permits the analysis and determination of multiple subpopulations of particles or cells in a greater quantity than the number of fluorochromes employed. Further, a greater number of cell subpopulations can be determined than the number of fluorescence detection channels, and associated electronic circuitry, utilized. In the present invention, a straightforwardly constructed instrument needs only two fluorescence channels that are capable of detecting distinct emission spectra of two different fluorochromes. On analysis in an apparatus as described above, cell subpopulations are distinguished by determining the ratio of the two distinct fluorochromes associated with each cell using only two fluorescence channels, each directed to detecting the distinct emission spectra of the fluorochromes. By using a ratio, many subpopulations of cells labeled with only two distinguishable fluorochromes or other marking agents can be determined. Moreover, in the flow-through cytometry techniques envisaged by the present invention, multiple cell subpopulations can be detected in rapid order from a single sample of cells. The present invention not only provides for the detection of multiple subpopulations of cells, but also provides for the simultaneous enumeration of the cells so detected. Furthermore, by reliance upon a ratio of signals detected with respect to each cell or particle, they are distinguished by the ratio parameter which is independent of the quantity of fluorescence marking agents bound to a cell; in addition, cell subpopulation distributions do not overlap each other to cause erroneous or inaccurate results. An additional advantage is that it is possible to detect the nonspecific binding of fluorescenated agents to particles.

BRIEF DESCRIPTION OF THE DRAWINGS

FIG. 2 is a graphic representation of multiple subpopulations of particles determined by a ratio distinction technique in accordance with the principles of the present invention.

DETAILED DESCRIPTION

Figure 1:
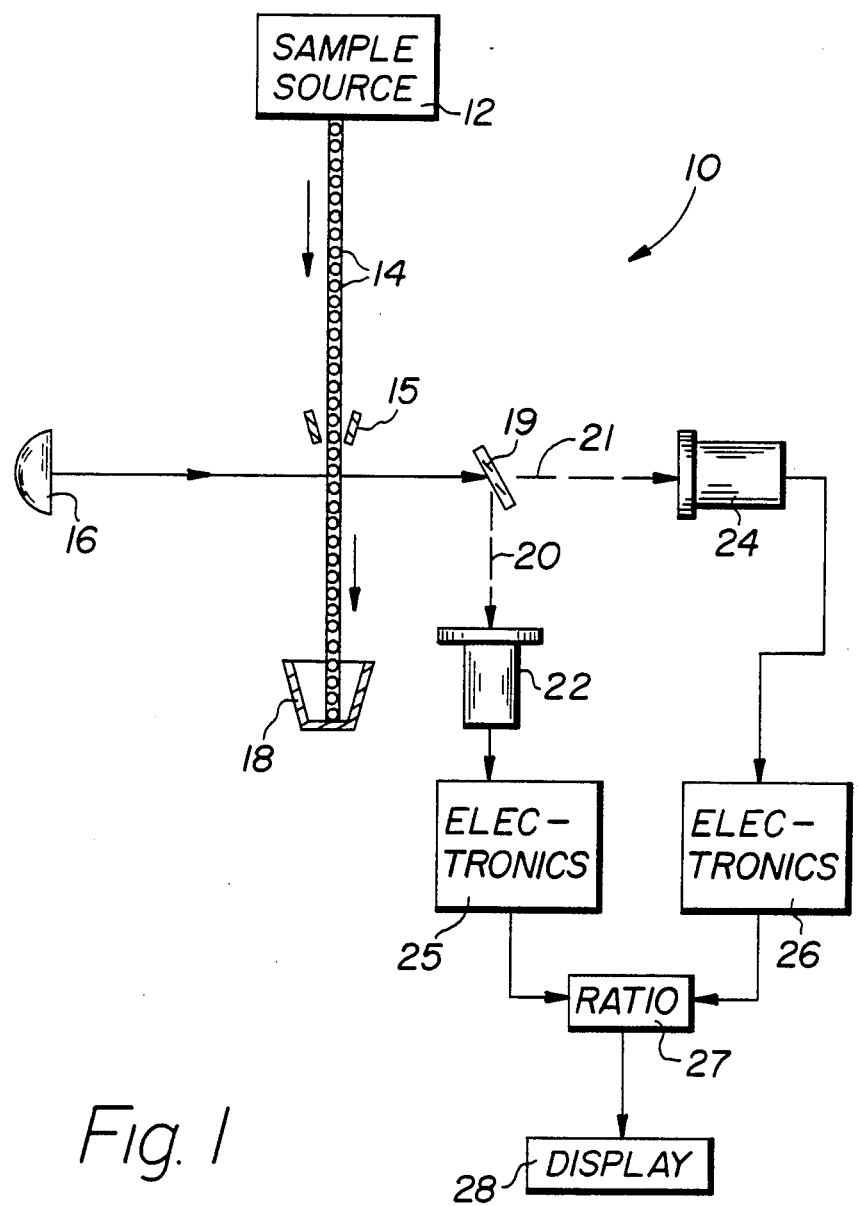
FIG. 1 is a schematic representation of a cytometric apparatus for detecting two fluorescence characteristics of individual particles moving in a flow path from the sample source.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Referring to the drawings, and FIG. 1 in particular, there is illustrated a schematic representation of a cytometric apparatus 10 for detecting cells, or other particles, having particular parameters. Before any particules are analyzed in detection apparatus 10, they are treated with a plurality of marking agents that have quantifiable marking characteristics, preferably different from each other. For example, in tests wherein cells are to be classified, it is most advantageous to work with antibody proteins. In general, these antibody proteins are labeled with two marking agents, preferably fluorochromes, although three or more such agents may be utilized. Each fluorochrome has distinct emission and/or excitation spectra in specifically defined color bands. The fluorochromes are bound to antibody proteins such that the number of these proteins labeled with each fluorochrome form a known ratio. By labeling different antibody proteins, each being specific for receptors on a certain cell type, with different ratios of fluorochromes, a plurality of these differently labeled antibodies can be mixed together and reacted with a cell population in a sample mixture. Each antibody, with a known ratio of fluorochromes attached thereto, will then bind to those cells having specific receptors therefor, thereby labeling subpopulations of cells. Once this treatment has been completed and specific cell subpopulations labeled, the cell sample is placed in a sample source 12 associated with detection apparatus 10 as seen in FIG. 1.

Before explaining the operation of detection apparatus 10, in general terms the two fluorochromes, or other marking agents if so used in conjunction with this invention, may be applied to the receptive substances such as antibody proteins in different pre-selected ratios. These ratios range between zero percent and one hundred percent of each fluorochrome; i.e., there may be no fluorochrome of the first type on an antibody protein, while there is one hundred percent of a fluorochrome of the second type on that same antibody protein. Of course, various ratios of the two fluorochromes lying between the extremes of zero percent and one hundred percent fall within the purview of the present invention. Furthermore, present cytometric techniques and equipment used therefor should allow the detection of at least five different cell subpopulations using the method and apparatus as described herein. It is understood, however, that more than five cell subpopulations may be distinguished by the present method and apparatus, but the quality of the signal may not be as strong for more than five ratio measurements. Further, the use of three or more fluorochromes significantly increases the number of distinguishable ratios which are possible with the present invention.

Turning now to the specifics of detection apparatus 10 in FIG. 1, sample source 12 contains the substances, such as cells, which have been treated with different marking agents, such as fluorochromes, in a plurality of different preselected ratios. For the ensuing discussion, two such fluorochromes are employed to treat the cells, merely for exemplary and descriptive purposes. The treated cells 14 are delivered in a fluid stream, preferably individually, to and through sensing region 15, such as an orifice, which will allow the optical aspects of the cells to be detected. Sensing features are well-known in flow-through cytometric devices, and one such sensing arrangement is disclosed in an article by Thomas, R. A., et al. "Combined Optical and Electronic Analysis of Cells with the AMAC Transducers," The Journal of Histochemistry and Cytochemistry, Vol. 25, No. 7, pages 827–835, 1977. As each treated cell 14 passes through sensing region 15, light from a light source 16 is directed at the cells. Light source 16 delivers light to the cells and may include lasers, Mercury or Xenonarc lamps, or the like, capable of emitting a number of lines through a wide range of color regions. Also, the light from light source 16 in the embodiment being described should be sufficient to cause excitation of the two different fluorochromes used to treat cells 14. Thus, when the light strikes each cell 14 the fluorochromes bound thereto become excited thereby providing a mechanism for distinguishing the fluorescence characteristics of each cell. It is appreciated that when fluorochromes are selected having different excitation ranges, it may be necessary to employ more than one light source to cover the disparate wavelengths of excitation.

As each cell passes through the sensing region it is then collected in a receptacle 18; although not shown herein, the cells could be sorted according to known sorting techniques wherein subpopulations of cells can be collected separately. Fluorescent light from each cell, including fluorescence from up to two fluorochromes having distinct excitation spectra, is then directed to a dichroic mirror 19. The purpose of dichroic mirror 19 is to separate two different colors along the re-radiated light path generated by the fluorescence characteristics of each cell. In this fashion, the two different colors can be analyzed separately to thereby form a ratio as hereinafter described. Dichroic mirror 19 would be selected to separate, for example, the green from the red regions of the color spectrum. Wavelengths in the first color region would be reflected along optical path 20, while wavelengths of the second color region would be transmitted through dichroic mirror 19 along optical path 21. Each light path either reflected or transmitted through the dichroic mirror is then detected by fluorescence detectors 22 and 24, respectively, provided to receive the light energy separated into the two regions. Fluorescence detectors 22 and 24 may be conventional photomultiplier tubes which convert optical signals into electrical signals. These electrical signals are then fed to respective pulse processing electronics 25 and 26 wherein the electrical signals are processed for analysis purposes.

As part of this analysis, and preferably as part of the electronics of the apparatus herein described, a ratio of the electrical signals is determined. In the ratio determining means 27 the fluorescence signal from fluorescence detector 22 is related as a ratio to the fluorescence signal from fluorescence detector 24, or vice versa. Ratio means 27 thereby provides a mechanism to determine the fluorescence emitted by both excited fluorochromes associated with each cell and to establish the ratio of their fluorescence emissions. This ratio information is then fed to display means 28. The combination of the electronics 25 and 26, ratio means 27 and display means 28 are all preferably electrical circuits which will provide for various displays, information presentation, accumulation or recordation of the ratio of fluorescence signals associated with each cell being analyzed. The electrical components to provide analysis of the electrical signal relating to fluorescence may include state of the art technology and may vary according to the level of sophistication of the analysis and data presentation. One such electrical system for fluorescence determinations is described in U.S. Pat. No. 3,826,364.

Display means 28 preferably includes a screen to visually observe in graphic form the classification of each cell by subpopulation category. In addition, apparatus 10, along with the electronics and display may be designed to pre-program ratio information into the circuitry. For example, and referring now to FIG. 2, the electronics and display can be pre-programmed to include specifically defined fluorescence ratios along the x-axis of the screen. These ratios would include the same ratios of fluorochromes pre-selected to treat the antibody proteins which are specific for certain cell types. The Y-axis of the screen can be pre-programmed to plot the number of cells associated with the specifically defined ratios along the X-axis. In this fashion, a graphic, histogram representation of the subpopulations of cells classified into specific categories can be visualized and, if desired, recorded. As can be seen in FIG. 2, five subpopulations of cells have been identified having specific ratios of fluorescence, i.e., $<1/10$, $\frac{1}{3}$, $1/1$, $3/1$, and $>10/1$. The area under each of the cell type peaks, A to E, would provide the number of cells of that type measured. If desired, the electronics of this apparatus could be designed to calculate the approximate number of cells classified into each subpopulation.

It is appreciated that the present apparatus therefore provides for the classification of cell subpopulations and the numbers of cells in each subpopulation as a simultaneous determination, which can then be displayed to the operator. Moreover, because a ratio is used, cells are distinguished by this ratio technique independent of the quantity of fluorochrome-treated antibodies bound to a cell; as can be seen in FIG. 2, cell subpopulation distributions do not overlap because of the normalizing effect of the ratio. In making these classifications of cell subpopulations, windows 30 are provided around each pre-selected ratio which form a range for making the specific classifications. Upon analysis, the cells which fall within windows 30 on the ratio scale are taken to be specifically labeled; cells to which fluorochromes or other marking agents are non-specifically bound would provide ratios outside of the permitted windows, such as in the valley regions 31 between the peaks of the curve as seen in the graphic representation of FIG. 2. Accordingly, cells outside of windows 30, in valley regions 31, are taken to be non-specifically labeled and would be rejected electronically. However, non-specifically labeled cells provide ratios lying outside of the permitted ratio windows enabling separate enumeration of these cells.

Whereas FIG. 2, and the apparatus in general being described, distinguishes and classifies five different cell subpopulations, the number of cell types distinguishable by the method and apparatus of this invention may exceed five. However, signal strength should be adequate to resolve closer ratios, i.e., 9/1, 8/1, 7/1, etc. It should also be understood that the present method is most efficient when there is no cross reaction, i.e., each antibody protein labels only one cell type and each cell type accepts, for binding purposes, only one antibody protein type.

For illustrative purposes of the present invention the following examples exemplify, but do not limit the scope of, the mechanism for detecting and distinguishing multiple subpopulation of particles:

EXAMPLE 1

A fluorescent polymer is synthesized having pre-selectable proportions of two fluorochromatic monomers, in this case, fluorescein and rhodamine. Fluorescein will emit fluorescense when excited in the blue color region; on the other hand, rhodamine will emit fluorescense when excited in the yellow color region. Five polymer preparations are synthesized as follows:

Polymer Preparation 1—100% fluorescein, 0% rhodamine,

Polymer Preparation 2—75% fluorescein, 25% rhodamine.

Polymer Preparation 3—50% fluorescein, 50% rhodamine.

Polymer Preparation 4—25% fluorescein, 75% rhodamine.

Polymer Preparation 5—0% fluorescein, 100% rhodamine.

Antibody proteins which are specific for a certain cell type, herein designated as cell type A, are then labeled with Polymer Preparation 1; antibody proteins specific for cell type B are labeled with Polymer Preparation 2; antibody proteins specific for cell type C are labeled with Polymer Preparation 3; antibody proteins specific for cell type D are labeled with Polymer Preparation 4; and antibody proteins specific for cell type E are labeled with Polymer Preparation 5.

All of the conjugated (labeled) antibodies are mixed, and then the mixture is added to a cell sample. The cell sample includes cells believed to have specific receptors for the differently labeled antibodies. A-type cells would then be labeled with only the fluorochromes of Polymer Preparation 1, B-type cells with Polymer Preparation 2, C-type cells with Polymer Preparation 3, D-type cells with Polymer Preparation 4 and E-type cells with Polymer Preparation 5.

On analysis in an apparatus such as described in FIG. 1, each treated cell is analyzed and its green fluorescein signal and red rhodamine signal are electrically detected and formed into a ratio as described in conjunction with apparatus 10 above. For A-type cells this ratio is greater than 10/1; for B-type cells the ratio is 3/1; for C-type cells the ratio is 1/1; for D-type cells the ratio is ⅓ and for E-type cells the ratio is <1/10. Thus, by determining the yellow/blue fluorescence ratio of each cell as it passes through the detection apparatus, it can be classified as belonging to one of the five cell types. A graphic representation of this classification is similar to that illustrated in FIG. 2.

EXAMPLE 2

Two polymer preparations are employed, one containing fluorescein only and another containing rhodamine only. The following preparations are prepared;

Preparation 1—100% of antibody protein is labeled with polymer containing fluorescein.

Preparation 2—75% of antibody protein is labeled with polymer containing fluorescein, and 25% of the antibody protein is labeled with polymer containing rhodamine.

Preparation 3—50% of antibody protein is labeled with polymer containing fluorescein, and 50% of antibody protein is labeled with polymer containing rhodamine.

Preparation 4—25% of antibody protein is labeled with polymer containing fluorescein, and 75% of antibody protein is labeled with polymer containing rhodamine.

Preparation 5—100% of antibody protein is labeled with polymer containing rhodamine.

When a mixture of these five antibody preparations is added to a mixed cell population (suspected of having specific receptors for the differently labeled antibody proteins), A-type cells accept only antibodies labeled with Preparation 1; B-type cells accept antibodies labeled with Preparation 2; C-type cells accept antibodies labeled with Preparation 3; D-type cells accept antibodies labeled with Preparation 4 and E-type cells accept antibodies labeled with Preparation 5. Upon analysis in a flow-through cytometer such as the apparatus of FIG. 1, data obtained is similar to that shown in Example 1.

EXAMPLE 3

The preparations of Example 2 are repeated, except that conventional PITC (fluorescein isothiocyanate) and RITC (rhodamine isothiocyanate) labeled antibodies are used in place of the fluorescein-containing and rhodamine-containing polymers. Results of analyzing these cells in a flow-through, dual fluorescence cytometer, would be substantially similar to the results shown in Example 1.

EXAMPLE 4

Microspheres are produced which contain preselected ratios of two fluorochromes having different emission characteristics. Microspheres may be produced in accordance with U.S. Pat. No. 3,790,492. The microsphere preparations are then substituted for the polymer preparations of Example 1. On flow-through analysis, the data obtained is similar to that shown in Example 1.

EXAMPLE 5

Microspheres similar to those in Example 4 are prepared in which fluorescein-containing microspheres and rhodamine-containing microspheres are substituted for the two types of polymers listed in Example 2. Upon analysis in a flow-through cytometer, the data obtained is substantially similar to that shown in Example 1.

Thus, the present invention provides a method and apparatus for detecting and distinguishing multiple subpopulations of particles in a larger particle population. Advantageously, many more subpopulations may be distinguished than the number of fluorescence agents and fluorescence channels employed in this invention. By utilizing a ratio of fluorescence signals, particle subpopulations can be detected and classified, while at the same time enumerating the number of particles classified into each particle subpopulation.

What is claimed is:

1. A method of distinguishing multiple subpopulations of cells comprising:
    labeling antibody proteins of the same specificity with two fluorochromes in a pre-selected ratio and employing the same two fluorochromes in different pre-selected ratios to label antibody proteins with different specificities to thereby produce a plurality of differently labeled antibody proteins, each of said fluorochromes having distinct emission spectra;
    forming a mixture of said differently labeled antibody proteins;
    combining said mixture with a sample of cells believed to have specific receptors for said differently labeled antibody proteins;
    providing excitation energy to said cells by flow-through cytometry techniques to excite both types of said fluorochromes;
    analyzing each cell to determine the fluorescence emitted by both excited fluorochromes and to establish the ratio of the fluoroscence emissions; and
    classifying each cell into a subpopulation category by associating the established ratio of each cell with said pre-selected ratios.

2. The method of claim 1 wherein said antibody proteins are labeled by polymeric fluorochromes having pre-selectable proportions of fluorochromatic monomers.

3. The method of claim 1 wherein said antibody proteins are labeled by combining with each of a series of microspheres containing pre-selected ratios of said two fluorochromes.

4. The method of claim 1 which further includes the step of counting the number of cells classified into each subpopulation.

5. The method of claim 4 which further includes the step of counting the number of cells which do not fall within any defined subpopulation represented by the known, pre-selected ratios.

6. The method of claim 5 wherein the classification of cell subpopulations and numbers of cells within or without of each subpopulation are determined simultaneously and visually displayed to the operator.

7. A method of distinguishing multiple subpopulations of particles from a single sample of particles of a variety of types comprising:
labeling receptive substances of the same specificity with two marking agents in a pre-selected ratio and employing the same two marking agents in different pre-selected ratios to label receptive substances of different specificities to thereby produce a plurality of differently labeled substances, each agent having distinguishing, identifiable marking characteristics;
mixing said differently labeled substances with particles suspected of having specific receptors for said differently labeled substances; and
analyzing each particle to determine the ratios of the two identifiable marking characteristics associated with each particle so that each particle can be classified in a subpopulation category by associating the determined ratio of each particle with said pre-selected ratios.

8. A method of distinguishing multiple subpopulations of cells comprising:
labeling antibody proteins of the same specificity with two fluorochromes in a pre-selected ratio and employing the same two fluorochromes in different pre-selected ratios to label antibody proteins with different specificities to thereby produce a plurality of differently labeled antibody proteins, each of said fluorochromes having emission spectra and distinct excitation spectra;
forming a mixture of said differently labeled antibody proteins;
combining said mixture with a sample of cells believed to have specific receptors for said differently labeled antibody proteins;
providing excitation energy to said cells at each said distinct excitation spectra by flow-through cytometry techniques to excite both types of said fluorochromes;
analyzing each cell to determine the fluorescence emitted by both excited fluorochromes and to establish the ratio of the fluorescence emissions; and
classifying each cell into a subpopulation category by associating the established ratio of each cell with said pre-selected ratios.

9. A method of distinguishing multiple subpopulations of cells comprising:
labeling antibody proteins of the same specificity with more than two fluorochromes in a pre-selected ratio of any two of said fluorochromes and employing the same fluorochromes in different pre-selected ratios to label antibody proteins with different specificities to thereby produce a plurality of differently labeled antibody proteins, each of said fluorochromes having distinct emission spectra;
forming a mixture of said differently labeled antibody proteins;
combining said mixture with a sample of cells believed to have specific receptors for said differently labeled antibody proteins;
providing excitation energy to said cells by flow-through cytometry techniques to excite all of said fluorochromes;
analyzing each cell to determine the fluorescence emitted by the excited fluorochromes and to establish the ratio of the fluorescence emissions, and
classifying each cell into a subpopulation category by associating the established ratio of each cell with said pre-selected ratios.

10. A method of distinguishing multiple subpopulations of cells comprising:
labeling antibody proteins of the same specificity with more than two fluorochromes in a pre-selected ratio of any two of said fluorochromes and employing the same fluorochromes in different pre-selected ratios to label antibody proteins with different specificities to thereby produce a plurality of differently labeled antibody proteins, each of said fluorochromes having emission spectra and distinct excitation spectra;
forming a mixture of said differently labeled antibody proteins.
combining said mixture with a sample of cells believed to have specific receptors for said differently labeled antibody proteins;
providing excitation energy to said cells at each said distinct excitation spectra by flow-through cytometry techniques to excite all of said fluorochromes;
analyzing each cell to determine the fluorescence emitted by the excited fluorochromes and to establish the ratio of the fluorescence emissions; and
classifying each cell into a subpopulation category by associating the established ratio of each cell with said pre-selected ratios.

* * * * *